(12) United States Patent
Frommer et al.

(10) Patent No.: US 6,444,454 B1
(45) Date of Patent: Sep. 3, 2002

(54) METHOD FOR INCREASING THE GENE EXPRESSION OF SACCHAROSE SYNTHASE

(75) Inventors: Wolf-Bernd Frommer, Tübingen; Henning Schrader, Göttingen; Lothar Elling, Aachen, all of (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 09/486,291

(22) PCT Filed: Aug. 20, 1998

(86) PCT No.: PCT/EP98/05309
§ 371 (c)(1),
(2), (4) Date: May 19, 2000

(87) PCT Pub. No.: WO99/10511
PCT Pub. Date: Mar. 4, 1999

(30) Foreign Application Priority Data

Aug. 21, 1997 (DE) .......................................... 197 36 343

(51) Int. Cl.[7] .............................. C12N 9/00; C12N 9/10; C12N 9/24; C12N 1/20; C12N 15/00
(52) U.S. Cl. ...................... 435/193; 435/69.1; 435/183; 435/200; 435/252.3; 435/320.1; 435/419; 435/254.2; 435/254.21; 536/23.2; 536/23.6; 536/24.3
(58) Field of Search ................................ 435/69.1, 183, 435/193, 200, 252.3, 320.1, 419, 254.2, 254.21; 536/23.2, 23.6, 24.3

(56) References Cited

FOREIGN PATENT DOCUMENTS

| EP | 0 284 044 A1 | 9/1988 |
|---|---|---|
| EP | 0 717 107 A1 | 6/1996 |
| WO | WO 94/00574 | 1/1994 |
| WO | WO 94/01540 | 1/1994 |

OTHER PUBLICATIONS

Salanoubat et al. Molecular cloning and sequencing of sucrose synthase cDNA from potato: preliminary characterization of sucrose synthase mRNA distribution. Gene, 1987, vol. 60:47–56.*

Mahanty et al. High yield expression of the *N.crassa* plasma membrane H–ATPase in *S.cerevisiae*. J. Biol. Chem., 1994, vol. 269(26):17705–17712.*

Nitrogen Catabolite Regulation of Proline Permease in *Saccharomyces Cerevisiae* by Jean–Claude Jauniaux et al., FEBS 1987pp. 601–606.

* cited by examiner

*Primary Examiner*—Rebecca E. Prouty
*Assistant Examiner*—Manjunath N. Rao
(74) *Attorney, Agent, or Firm*—Herbert Dubno; Jonathan Myers

(57) ABSTRACT

The invention relates to a method for increasing the gene expression of saccharose synthase. To this end the invention provides for the expression of the saccharose synthase gene to be placed under the control of a proton-ATPase promoter. According to a preferred version of the invention gene expression of the saccharose synthase is also increased by increasing the number of copies of the saccharose synthase gene and of the proton-ATPase promoter.

15 Claims, 5 Drawing Sheets

METHOD FOR INCREASING THE GENE EXPRESSION OF SACCHAROSE SYNTHASE

FIELD OF THE INVENTION

The present invention relates to a method of increasing the gene expression of saccharose synthase, to a method of obtaining the saccharose synthase gene, to a new recombinant gene structure, to new vectors containing the recombinant gene structure, to transformed cells containing the recombinant gene structure and to the use of a saccharose synthase to split a dinucleotide.

BACKGROUND OF THE INVENTION

The saccharose synthase is an enzyme which is limited to plants. In many higher plants there are two different genes known per type; in the case of rice there are three different genes. The differ only slightly in their biochemical characteristics since they are equipped with different promoters and above all control the enzyme expression with precision at different development stages and organs of the plant. Thus in rice 8 days after germation the saccharose synthase 1 is especially located in the roots and stems, while the saccharose synthetic 2 is distributed throughout the entire plant.

Saccharose synthase 3 is especially active in rice grains and thus in a completely different life phase of the plant.

In the plant, the enzyme serves to split saccharose according to the following equation in which, in vivo exclusively the splitting reaction is of significance:

Splitting Reaction

Saccharose+UDP UDP-Glucose+Fructose

Synthesis Reaction

The saccharose serves as the transport form of the carbohydrate in plants and thus is split in their target cells, like cells of the storage organs, seeds, developing plant organs inn which the UDP glucose and fructose are directly usable. While the fructose must be initially stored for further use, the UDP glucose is directly available for the synthesis of starch and cellulose. Of economic and scientific interest both the splitting and synthetic directions of the enzyme can be considered. In the synthetic direction, a number of spatially similarly constructed sugars and nonsugars are accepted. In the splitting direction, derivatives of saccharose are accepted and in addition preferably the nucleoside diphosphates (NDPs) UDP, ADP and TDP. Thus a large number of saccharose-analysis disaccharides are available. These are interesting for research into the structure and functioning of glycoconjugates like glycolipids and glycoproteins. Since glycoconjugates also are involved in the communication of cells with one another, many of these structures are also of significance in medicinal research. The enzyme is recoverable from different plant sources. For the processing for example of rice seed, the seed must initially be swelled and then decomposed, the solid component largely filtered off and the filtrate prepurified on an ion exchange column. The large volume resulting from the column step is then reduced and subjected to a gel filtration. The active fractions are suitable for synthesis (compare for this purpose also DE 4 221 595.

The described recovery of saccharose synthase from rice grains is, however, problematical since rice grains have only a limited activity of 0.56 units per gram of dry weight. In addition, the purification is handicapped by the relatively high proportion of carbohydrate in the form of starch and cellulose which is present. Furthermore, the detrimental enzyme invertase, which splits saccharose, cannot be completely separated off. A reduction in the amount of the detrimental enzyme phosphate which decompose NDP's and the nucleotide sugar splitting enzymes which decompose NDP sugar is desirable. Furthermore, there is the disadvantage that the saccharose synthase in rice apparently is not a pure enzyme but is present in varying proportions of isoenzymes which apparently have different synthetic characteristics. Several syntheses of disaccharides can only be reproduced with difficulty with different enzyme charges. Since the isoenzymes follow different reaction kinetics, measurements of the kinetics are difficult. In addition, the isoenzymes cannot be separated from one another, since they are very similar to one another. Finally, the purification is very slow especially since only small fractions can be charged onto the gel filtration column. A shortening of the purification is thus desirable.

To avoid the aforementioned drawbacks, the method of choice is the use of a recombination microbial system. To be able to produce thereby relatively large quantities of enzyme in an economical and environmentally safe manner, expensive additives or poisons in the cultivation medium must be avoided. Furthermore, only a single saccharose synthase gene can be permitted to be expressed. In the sense of an accelerated purification, expression and/or activity of detrimental enzymes should be held as small as possible. Tests have already been conducted as to the expression of a saccharose synthase gene from *Solanum tuberosum*, Salanoubat, M. and Belliard, G.: molecular cloning and sequencing of sucrose synthase DNA from potato (*Solanum tuberosum L.*) preliminary characterization of sucrose synthase mRNA distribution, in: Gene 60, 47–56, 1987) in the *Saccharose cerevisiae* strain YSH Riesmeier, J. W., et al.: isolation and characterization of a sucrose carrier DNA from spinach by functional expression in yeast. EMBO J 11 (13), 4705–4713, 1992).

For this purpose, the gene is cloned in plasmid 128A2 under control of the ADH promoter (see FIG. 1) and then transformed in the mentioned yeast strain. The ADH promoter normally regulates the reading frequency of the yeast enzyme alcohol dehydrogenase which is constitutively expressed and thus is always provided with exactly equal amounts in the organism. In this manner, the saccharose synthase is expressed with similar expression characteristics under the control of this promoter. This expression results in parts to the yeast strength, indeed the capacity, to split saccharose. However, the specific activity is relatively small: depending upon the method of determination, 5 to 25 mU saccharose synthase/mg of protein can be determined.

OBJECT OF THE INVENTION

It is therefore the object of the invention to provide a method of increasing the gene expression from saccharose synthase by an increased proportion of enzyme. It is further an object of the invention to prepare a composition which can be used in such method.

SUMMARY OF THE INVENTION

The objects are achieved by a method in which the expression of the saccharose synthase gene is carried out under the control of a proton-ATPase promoter. The proton-ATPase promoter for this purpose is provided expressly ahead of the saccharose synthase gene. The gene stems preferably from *Solanum tuberosum* while the protein APTase promoter is preferably from yeast, especially *Sac-* charomyces cerevisiae. A further increase in gene expression is brought about in that the copy number of the saccharose synthase gene and the protein in ATPase promoter is increased. For this purpose, the gene is incorporated with the promoter in a gene construct, preferably in the plasmid pDR195 (compare FIG. 2) and the gene construct is then transformed in a microorganism, especially in the yeast strain *Saccharides cerevisiae* 22574d (Jauniaux, J.-C. et al. Nitrogen catabolite regulation of proline permease in *Saccharomyces cerevisiae*. Cloning of the PUT4 gene and study of PUT4RNA levels in wild-type and mutant strains, Eur. J. Biochem, 164, 601–606, 1987).

The recombinant enzyme is preferably purified additionally by means of ion exchange and ultrafiltration after decomposition of the cells. Since it is often required, for protein-chemical application, to prepare very pure protein, the further purification of the technical enzyme preparation can include especially an additional purification step on chelating sepharose.

The saccharose synthase obtained according to the method of the invention can be used for the splitting of disaccharides (for example 2-desoxysaccharose) or N-acetylsaccharosamine with UDP. The enzyme can also be used for the splitting of saccharose with ADP.

The recombinant enzyme is generally usable precisely like the enzyme from rice (see Patent DE 4 221 595). The invention is described in greater detail hereinafter based upon an example.

EXAMPLE

1. Cloning, transformation and expression of saccharose synthase forming *Solanum tuberosum* in *Saccharomyces cerevisiae* strain 22574D.

Figure 1:
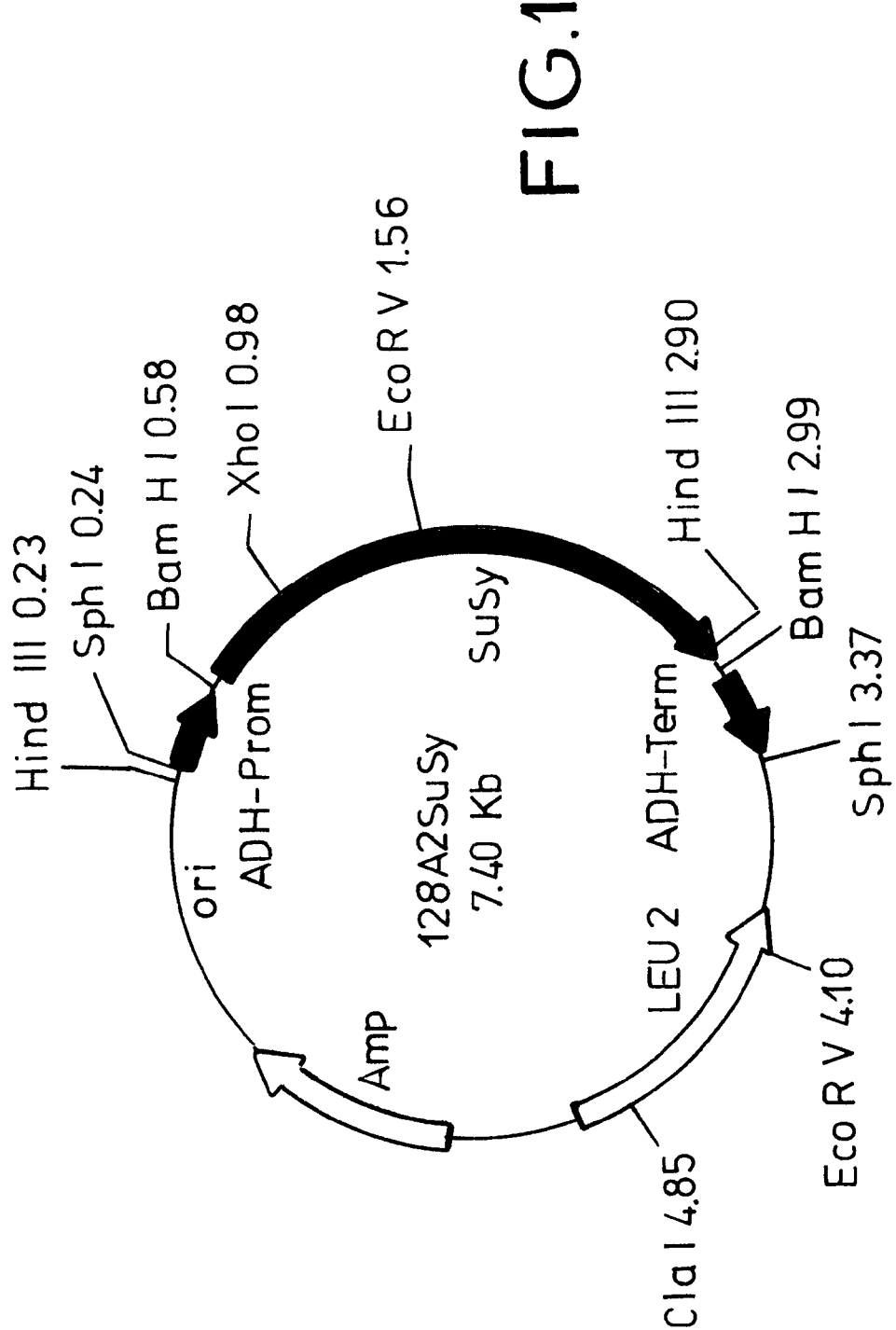
FIG. 1 is a map of the plasmid 128 A2, SUSy.

From the plasmid 128 A2, SUSy (FIG. 1) the susI gene is cut out by means of the restriction enzyme $BamH_I$. The cut products are electrophoretically separated in an agarose gel and the susl gene is cut out by means of the restriction enzyme BamH1. The cut products are electrophoretically separated in an agarose gel and the susl sequence is cutout from the latter and eluted.

Figure 2:
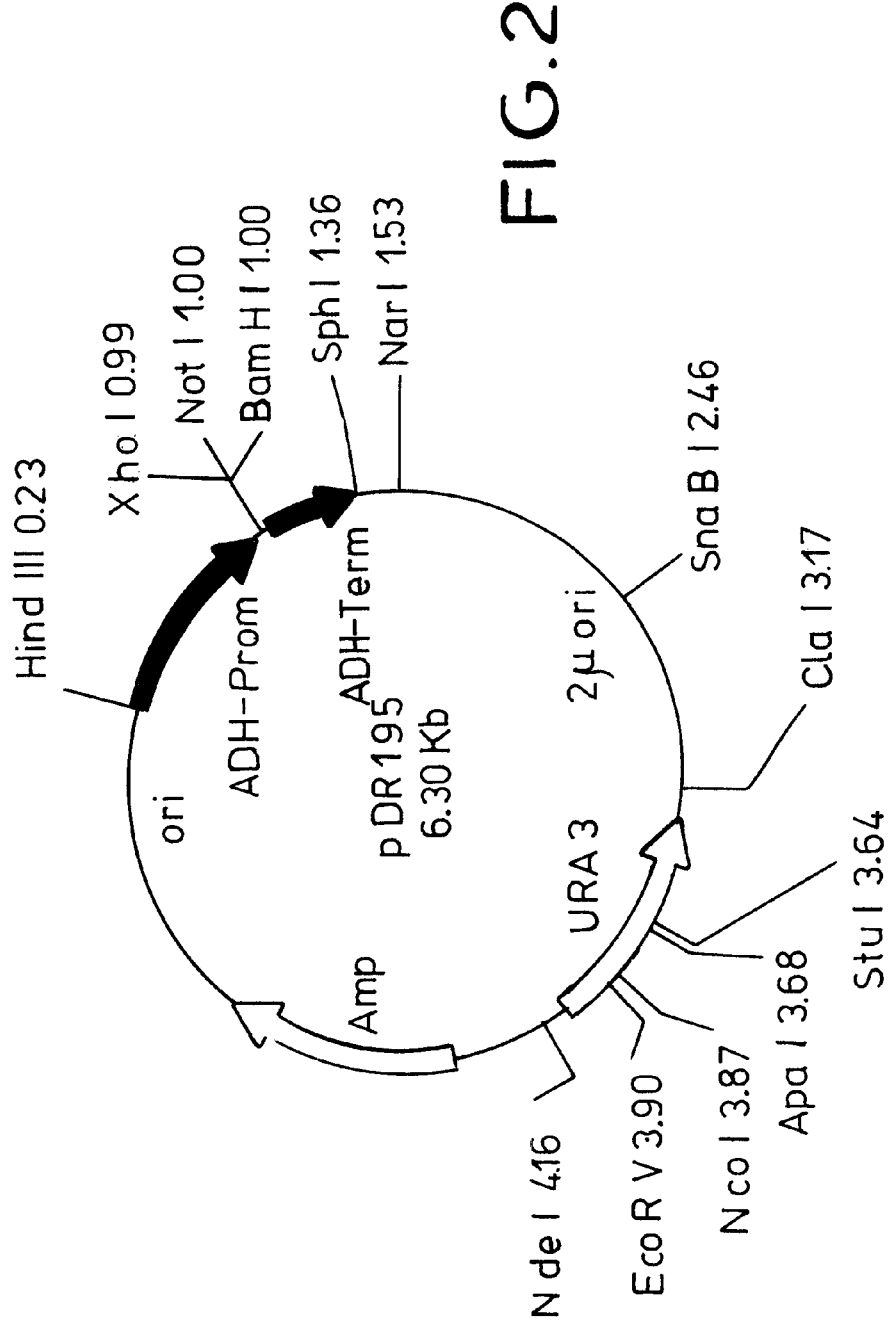
FIG. 2 is a map of the plasmid vector PDR 195.

The vector PDR195 (FIG. 2) is also cut by means of the restriction enzyme BamH1. The product is then purified by a phenylaztion, precipitated with ethanol, redissolved and dephosphyrylated with alkali phosphatase. The alkali phophetase is deactivated within a period of 30 min with 50 mM EDTA at 65° C. It is phenolated anew and then precipitated with ethanol.

Figure 3:
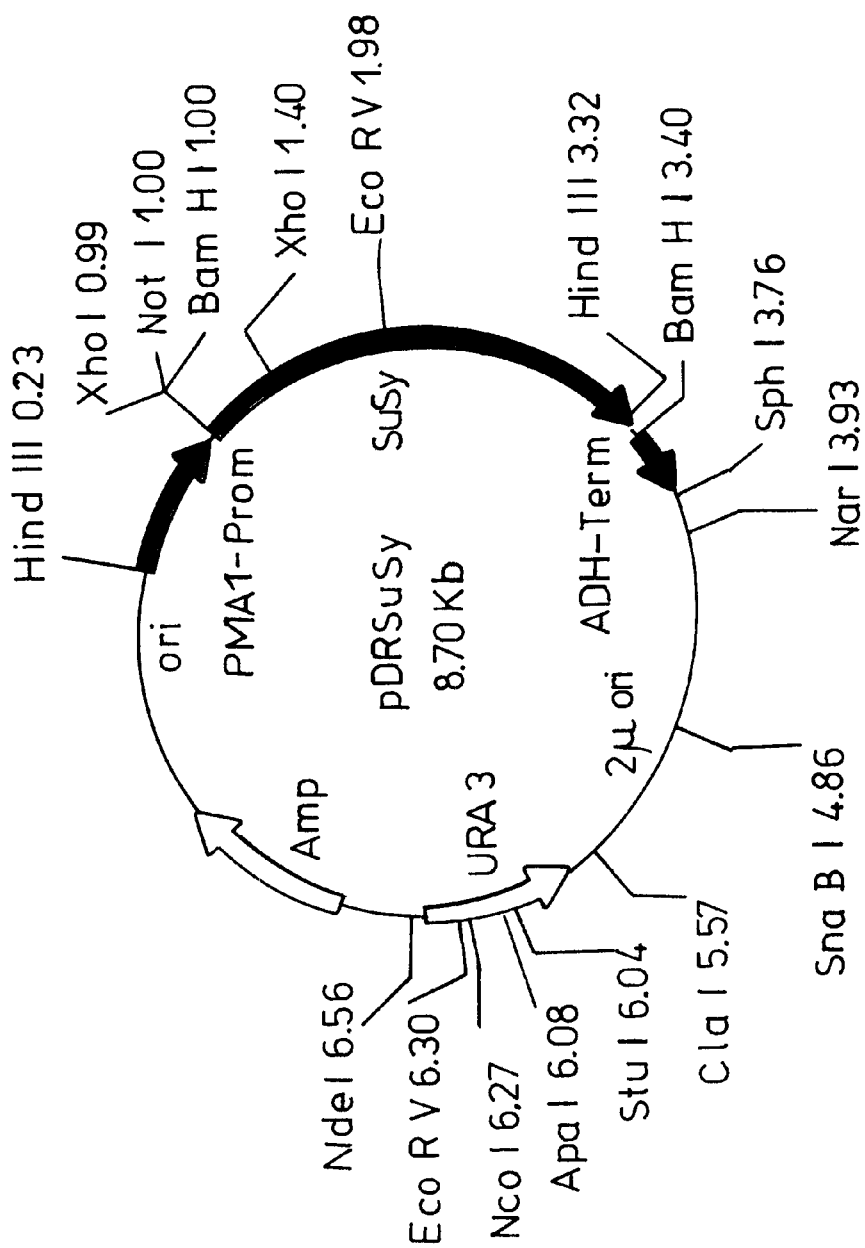
FIG. 3 is a map of Plasmid pDRSuSy.

About 200 µg of the vector and about µg of sus1 sequence are ligated overnight at 16° C. with T4 Ligase. The ligation product is transformed in competent *E. coli* cells strain DH5 alpha and individualized in this manner and multiplied on selective medium. These *E. coli* colonies were taken up in 3 ml aliquates and utilized in a plasmid preparation. The plasmids are each cut with the restriction enzymes BamH1, $BamH_{I+Xhol}$, hind III and the cut product is electroferetically separated on an agarose gel. With the aid of a band pattern the respective plasma constructor which contain the susl sequence in the desired orientation can be identified. They are indicated as pDRSuSy (FIG. 3). An associated *E. coli* strain is selected and introduced in 3 ml units in order to enable the recovery of sufficient plasmid for the transformation of the yeast cells.

For transformation of the yeast cells, initially a competent yeast must be provided. For that purpose the following general protocol is used.

The following solutions are produced and sterilized (Sterile fertilization can be used; it is also possible to carry out sterilization for 15 minutes in an autoclave at 121° C.).

Solution A:
 10 mM Bicine pH 8.35
Solution B:
 200 mM Bicine pH 8.35
 40% peg 1000
Solution C:
 10 mM Bicine pH 8.35
 150 mM NACL The yeast cells are soaked overnight at 30° C. and at 200 revolutions per minute –5YPD Medium

| 10 g | Yeast Extract |
| 20 g | Peptone |
| 20 g | Glucose in one liter distilled water. |

The 5 ml cultures are completely transferred to 200 ml YPD which has been heated to 30° C. At this temperature and 120 revolutions per minute, the culture after about 3 hours has an $OD_{600}$ of 0.6. The culture is centrifuged for 10 minutes at 4000 revolutions per minute and 4° C. and washed on ice with 30 ml of solution A. Under the same conditions, the composition is centrifuged again and the cells taken in 2 ml of solution A. Each 200 µl is aliquoted and frozen in a cabinet at −70° C. After 60 minutes that are usable and remain usable for several months.

For the transformation, 1–2 µg of the plasmid is mixed with 50 µg of herring sperm DNA in 10 µl of water and this solution is introduced to an aliquote of the frozen cells. The composition is shaken at 37° C. for 5 minutes. Then 1 ml of solution B is supplied and the system is incubated at 30° C. under the aforementioned shaking for 60 minutes. The cells are then centrifuged for two minutes at 3000 revolutions per minute, the pellet is washed with 500 µl of solution C and centrifuged again. The pellet is then taken up in 100 µl of solution C.

This suspension is plated on SD solid medium with 2% glucose. The yeast of the strain 22574D thus is formed with the plasmid pDRSuSy is allowed to grow for two days at 30° C. on plates. The colonies which resulted were multiplied on SD medium with 2% glucose. In addition, these colonies were cultured in liquid SD medium to a stationary phase (30° C., 120 rpm shaking speed), the cells decomposed and the resulting extract by comparison with the extract from nontransformed cells was electrophoretically separated on a 10° SDS in polyacrylamide gel. In parallel, the extract was measured with an enzyme test (Elling, L. and Kula, M.-R.:

Purification of Sucrose Synthase from Rice and its Protein-Chemical Characterization, in: J. Biotechnol. 29, 277–286, 1993).

The polyacrylamide gel supplied a 90,000 kD band of the transform cells which was not found in the nontransformed product. A band of this size is expected for the monomer of saccharose synthase. The enzyme test provided a significant activity of the extract of the transformed cells. By comparison, the activity of the nontransformed cells was below the detection limit.

Since the cells of the gene were consecutively expressed, no expression harvest time point had to be observed. For the ten liter culture volume, the following procedure was used:

From the maintenance culture which is plated out anew monthly, a colony is selected and taken up in a sampling tube with 3 ml SD-2% glucose after about 24 hours the culture has grown (all conditions relate to 30° C. temperature and 120 rpm shaking speed. The culture is fed into 50 ml of the same medium and incubated anew for 24 hours. Finally, the 50 ml culture is fed to 250 ml of the medium and shaken for a further 24 hours. With the 25 ml seed, 5 times 2L SD-2% glucose is added and the culture grown to completion (overnight to –$OD_{600}$ of about 3.5 to 4.0).

The cells were harvested by centrifugation taken up in 200 mM HEPES pH 7.6 in a ratio of 4:6 (w/w) and can be directly used or stored for several months at –20° C.

2. Purification of the recombinant saccharose synthase the cells taken up in 200 mM HEPES pH 7.6 are milled in a glass bead milled for 20 min at 4000 rpm stirring speed. The glass speeds used had a diameter of 0.5 mM. During and after milling, the suspension is held on ice. Finally, the solids component is separated off by a centrifugation at 15,000 pm and 4° C. over a period of 15 min. The saccharose synthase is thereafter purified by means of an ion exchange chromatography. The chromatographic apparatus was comprised of a column with 300 ml Q-sepharose ff, a P1 pump, a P1 pump, a detector UV-1 (200 nm), a fraction collector Frac300 and a recorder REC101. All of the materials came from Pharmacia.

The column was equilibrated with 1 liter 50 mM HEPES-NaOH pH 8.0 (standard buffer) at a flow rate of 10 ml per minutes. The flow velocity was held constant for all further steps.

Then followed the charging with centrifugation supernatant whereby material from the five liter culture was added. Unbound protein was washed out with one liter standard buffer with 0.1 MKCl.

The salt gradient was started with buffer A (standard buffer with 0.1 MKCl) and buffer B (standard buffer with 0.4 MKCl) The total volume of the gradient amounted to 1 liter although it can extend also to 1.5 liter. In the region between 0.2 and 0.3 MKCl, the saccharose synthase was eluted.

The column was regenerated by the following rinsing plan:

500 ml 0.1M potassium acetate, pH 4.0 with 1 M NaCl, 1 liter water, 300 ml 2M NaOH; 1 liter water; 500 ml 50 mM HEPES pH 7.6 with 1M NaCl; 1 liter water. For storage at 4° C., the gel was placed in 20% ethanol. The saccharose synthase containing fractions were combined and reduced successively in 50 ml ultrafiltration cells of the firm Amicon. The membrane was Amicon YM30 (exclusion molecular weight (30,000 d), diameter 43 mM.

Per run of a 300 ml Q-sepharose FF-column, 10 to 50 ml of the reduced product can be obtained. The preparation obtained is usable for synthase. For research on the protein itself, the recombinant saccharose synthase was then subjected to further purification on chelating sepharose. For that purpose, the gel material chelating sepharose fast flow from Pharmacia was used.

The column packed with 50 ml of gel material was equilibrated with three volumes of 1M NaCl in 0.1M sodium acetate pH 4.0. Then in the same buffer 0.1M copper sulfate was dissolved and rinsed through the column until the column was colored uniformity blue. Excess copper sulfate was washed down with three column volumes of 1M NaCl in 0.1 M sodium acetate pH 4.0.

Before the example is applied, the column is equilibrated as follows:

Initially it is flushed with 150 mM KCl in 200 mM HEPES pH 7.2 and then with 3 column volumes each of this buffer and 10 mM imidazole and finally with this buffer and 1 mM imidazole. The sample or protein solution is brought to a concentration of 1 mM imidazole and then pumped over the column. Unbound protein is washed from the column with 1 mM imidazole in 150 mM KCl and 200 HEPES pH 7.2. The elution of the bound protein is effected with an imidazole gradient of 1 mM to 70 mM in 150 mM KCl and 200 mM HEPES pH 7.2. Most of the protein appears at 20 to 30 mM imidazole while the saccharose synthase appears at 30 to 55 MM.

With the aid of subsequent washing step with 100 mM imidazole in 150 mM KCl and 200 mM HEPES pH 7.2, the column is brought into condition for the next use. If a further use is not desired, the copper is washed out with three column volumes of 50 mM EDTA in water. The material is them in its starting condition. It can be stored in 20% ethanol 4° C.

With the aid of this cleaning process the further purification arrives at a preparation of 2.4 U saccharose synthase/mg protein with 6.5 u/mg protein with a yield of 82%. This corresponds to a purification factor of 2.7. In total, 96% of the initial activities can be found in the Eluaat.

Table 1 shows a comparison of the purification schemes for yeast and rice. The following steps of ion exchange chromatography and ultrafiltration are identical for yeast and rice.

The chromatography on Q-sepharose FF, the ultrafiltration on membranes with a cut off 30,000 da. The rice preparations must then be finely purified on a gel filtration column in order to remove invertase which may still be present, although this process is not fully successful. This can give rise to undesired decomposition reactions of the product upon application of the saccharose synthase in synthesis. By contrast, yeast contains no invertase when it is cultured on a saccharose free medium. A fine purification by gel formation is therefore not necessary. This saves material, accelerates the purification process and increases the yield of enzyme and thus has also an economic advantage.

Table 2 shows a comparison of two preparations from yeast and rice according to the purification schemes of Table I: The activity contained in the biomass is by a factor of 10 greater with yeast than with rice. The specific activity of the enzyme in the raw product is correspondingly higher also. Since the columns used in the subsequent processing steps are limited in their charging capacity by the amount of protein to be applied, a greater quantity of enzyme can therefore be purified per column run.

After ion exchange and ultrafiltration, the recombinant enzyme from yeast is cleaner than the enzyme from rice. It is important, however, that the preparation of the recombinant enzyme no longer contains any relevant quantities of by-product activity. For the enzyme from yeast, the purification is concluded with a total yield of 40%. By comparison, the rice preparation must be subjected to a gel filtration step which increases the cleanliness by a factor of 10 but cannot satisfactorily remove by-product activity. As a consequence, the yield for the total purification drops to 11.3%.

Table 3 compares the side activities of the described enzyme preparations of yeast and rice. As Table 1 shows, the cleaning of the recombinant enzyme from yeast encompasses four steps while the cleaning of rice encompasses five steps. In both cases, the NDP decomposing phosphatase are completely removed. The invertase is not present in the yeast preparation because of the culture conditions but in the preparation from rice is present in such amounts that several flow synthase reactions are sharply disturbed since the invertase decomposes the synthase product. UDP glucose decomposing activity is present in the preparation from yeast in very small quantities.

3. Saccharose splitting with recombinant saccharose synthase.

Initially the acceptance of the recombinant saccharose synthase for different NDP's in saccharose splitting was investigated. The reaction conditions was as follows:

| NDP Concentration | 1.6 mM |
|---|---|
| Saccharose: | 500 mM |
| Saccharose Synthase: | 0.035 U |
| Buffer (HEPES-KOH, pH 7.6): | 200 mM |
| Volume: | 1 ml |

Figure 4:
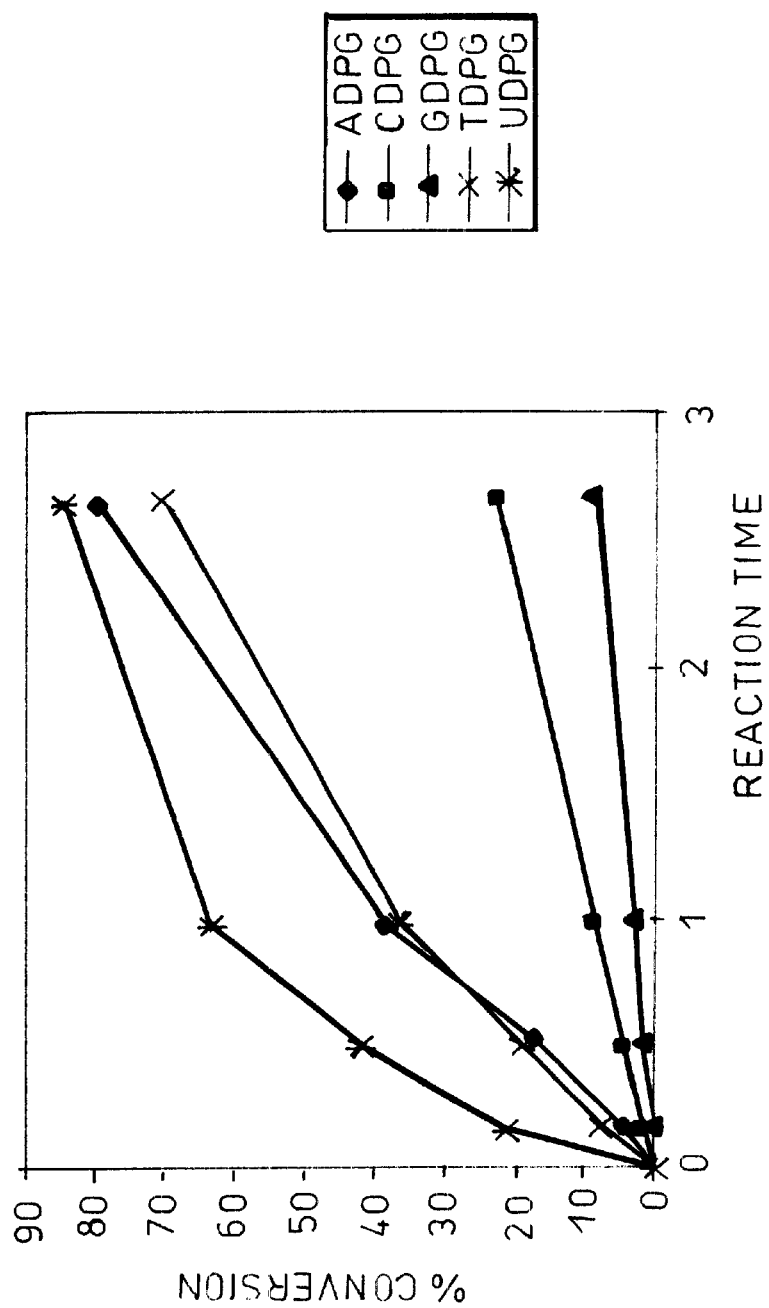
FIG. 4 is a graph comparing the reaction times of the splitting of saccharose by the nucleotide diphosphate (NDPs) ADP, CDP, GDP, TDP and UDP into the respective NDP-glucoses and fructose using the sucrose synthase obtained according to the invention to catalyze the reaction.

The reactions with different NDP's were carried out at a temperature of 30° C. The results are shown in FIG. 4. The acceptance of NDP's in saccharose splitting as a function of reaction time was found to correspond to the following sequence:

UDP>ADP=TDP>CDP>GDP

In addition, the Michaelis-Menten-Kinetics of the saccharose splitting with the recombinant saccharose synthase with UDP as a function of saccharose was determined.

The reaction condition for this were as follows:

| UDP Concentration | 1.6 mM |
|---|---|
| Saccharose Synthase: | 14 mU |
| Buffer (HEPES-KOH, pH 7.6): | 200 mM |
| Volume: | 1 ml |

The reactions were carried out at a temperature of 30° C.; the reaction time amounted in each case to 10 minutes.

Figure 5:
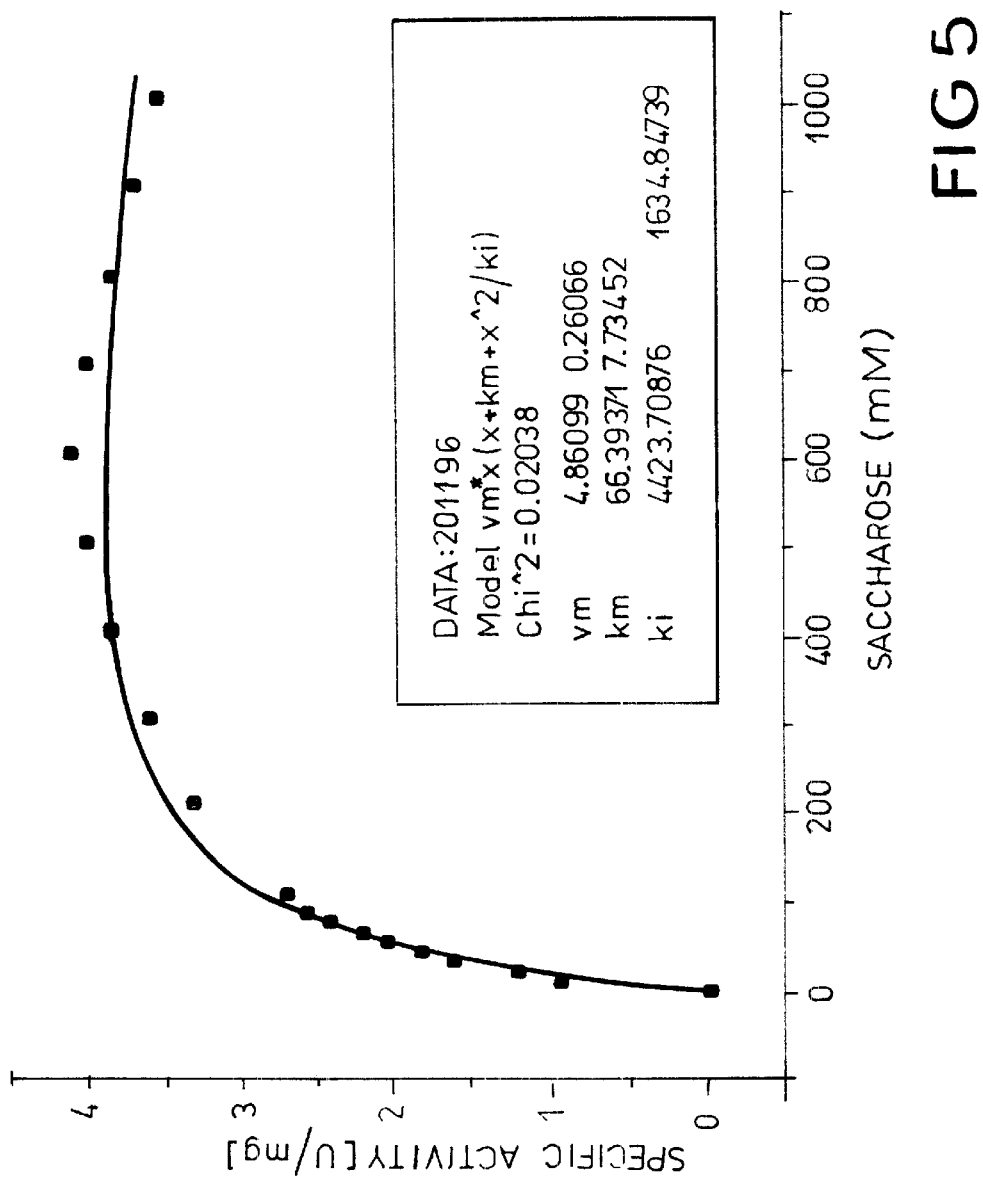
FIG. 5 is a graph plotting the concentration of saccharose against the specific activity of the saccharose synthase used to catalyze the splitting of the saccharose to show the Michaelis-Menten Kinetics of the splitting reaction.

In FIG. 5, the Michaelis-Menten-Kinetics of saccharose synthase as a function of saccharose concentration is shown. The illustration shows a Km for saccharose of 66 mM. The concentrations of more than 600 mM saccharose substrate excess limiting sets in.

4. Syntheses of selected Nucleotide sugars with recombinant saccharose synthase.

The described syntheses below of ADP-glucose-2-desoxyglucose and UDP-N-acetyl glycocyamine following the splitting direction of the enzyme with ADP or UDP.

4.1 Synthesis of ADP glucose.

For the synthesis of ADP glucose, the following reaction composition is used:

| AMP: | 4 mM |
|---|---|
| ATP: | 4 mM |
| Recombinant Saccharose | |
| Synthase: | 100 U |
| Myokinase from Rabbit | |
| Muscle: | 10 U |
| BSA: | 100 mg |
| MgCl$_2$: | 0.125 |
| Buffer A: | 100 ml |
| Buffer A: HEPES-NaOH, pH 7.5: | 200 mM |
| Saccharose: | 500 mM |
| DTT: | 3 mM |

The reaction composition was sterile filtered and stirred overnight at 30° C. On the next day, the reaction solution was reduced in an Amicon cell type 8050 with a YM 10 membrane (cut off of 10,000 d). The protein remains in the composition while the reaction products are drawn off. The composition was replenished with 90 ml of the following substrate solution:

| AMP: | 4 mM |
|---|---|
| ATP: | 4 mM |
| MgCl: | 0.125 mM |

Buffer A, sterile filtered, and a new reaction is carried out overnight.

These are repeated 10 times. In the course of the reaction repetition, 10 U myokinase are after added.

In this way, 2.8 g ADP-glucose with a yield of 55% with respect to the AMP and ATP used was made. The total yield of the synthase after purification amounted to 2.2 g corresponding to 43.6%.

4.2. Synthesis of MDP-2-desoxy glucose and UDP-N-acetylglucosamine.

For the synthase of UDP-2-Desoxyglucose and UDP-N-Acetylglucoseamine, the following reaction composition is used.

| Disaccharide: | 250 mM |
|---|---|
| UDP: | 2 mM |
| Saccharose Synthase: | in different amounts |
| HEPES-NaOH, 7.6: | 200 mM |
| Volume: | 1 ml |

The reaction mixture is incubated for 24 hours at 30° C. and the reaction stopped at 95° over a period of 5 minutes.

In this manner, 0.11 U saccharose synthase 5.9% of the two desoxy saccharose was split off.

With 1.25 U of the enzyme, 12.4% of the N-acetyl saccharosamine can be converted.

TABLE 1

Comparison of the Purification Schemes of Yeast and Rice

| Yeast | Rice |
|---|---|
| Decomposition | Decomposition |
| Centrifugation | Filtration |
| Ionexchange | Ionexchange |

TABLE 1-continued

Comparison of the Purification Schemes of Yeast and Rice

| Yeast | Rice |
|---|---|
| Ultrafiltration | Ultrafiltration |
| | Gelfiltration |

TABLE 2

Comparison of the processing data of Yeast and Rice

| | Yeast | Rice |
|---|---|---|
| Activity per Gram Cells or rice grains | 6.2 U/g | 0.56 U/g |
| Specific Activity in the raw decomposed product | 0.22 U/mg Protein | 0.07 U/mg Protein |
| Specific Activity after Ionexchange and ultra-filtration | 2.4 U/mg Protein | 1.4 U/mg Protein |
| Specific Activity at the end of purification | 2.4 U/mg Protein | 13.6 U/mg Protein |
| Yield Full Purification | 40% | 11.3% |

TABLE 3

Comparison of the side activities

| Side Activities | Yeast in 4 Steps | Rice in 5 Steps |
|---|---|---|
| Phosphatase | 0 | 0 |
| Invertase | 0 | 0.05% |
| UDP Glucose Decomposition | 0.0018% | 0.05% |

What is claimed is:

1. A process for increasing gene expression of saccharose synthase in which the expression of the saccharose synthase gene is carried out in a transformed yeast cell containing a saccharose synthase gene wherein the saccharose synthase gene is under the control of a proton-ATPase promotor derived from yeast and capable of producing saccharose synthase having an activity of about 6.2 U/g of yeast cells or of about 0.22 U/mg of total protein in the raw decomposed yeast cells and in which the saccharose synthase is free from invertase activity.

2. A process according to claim 1, characterized in that the proton ATPase promotor is connected ahead of the saccharose synthase gene.

3. A process according to claim 1 characterized in that the saccharose synthase gene is derived from *Solanum tuberosum*.

4. A process according to claim 1, characterized in that the proton ATPase promotor is derived from *Saccharomyces cerevisiae*.

5. A process according to claim 1, characterized in that the gene expression of the saccharose synthase is additionally elevated by increasing the copy number of the saccharose synthase gene linked to the proton ATPase promotor.

6. A process according to claim 5, characterized in that the increase in the gene expression is obtained by increasing the gene copy number, and by incorporating the gene and the promotor in a gene construct.

7. A process according to claim 6, characterized in that *Saccharomyces cerevisiae* is the yeast transformed with the gene construct.

8. A process according to claim 7, characterized in that the strain 22574d is the yeast transformed with the gene construct.

9. A process according to claim 1 characterized in that the saccharose synthase is purified to remove a nucleotide phosphatase.

10. The saccharose synthase gene preceded by a proton ATPase promotor obtained from a yeast and capable of producing saccharose synthase having an activity of about 6.2 U/g of yeast cells or of about 0.22 U/mg of total protein in the raw decomposed yeast cells.

11. The saccharose synthase gene according to claim 10 wherein the saccharose synthase gene is from *Solanum tuberosum*.

12. The saccharose synthase gene according to claim 10, characterized in that the proton ATPase promotor is from *Saccharomyces cerevisiae*.

13. A transformed yeast cell containing a saccharose synthase gene preceded by a proton ATPase promotor from a yeast in replicated form according to claim 10.

14. A transformed yeast cell according to claim 13 wherein the yeast is *Saccharomyces cerevisiae*.

15. A process for increasing gene expression of saccharose synthase in which the expression of the saccharose synthase gene is carried out in a transformed *Saccharomyces cerevisiae* yeast cell containing a saccharose synthase gene derived from *Solanum tuberosum* wherein the saccharose synthase gene is under the control of a proton-ATPase promotor derived from *Saccharomyces cerevisiae* and in which the saccharose synthase is free from invertase activity.

\* \* \* \* \*